(12) United States Patent
Rennie

(10) Patent No.: US 10,717,686 B2
(45) Date of Patent: Jul. 21, 2020

(54) SELF-LIGHTING PALO SANTO COMBUSTIBLE ARTICLE AND METHOD OF MANUFACTURE THEREOF

(71) Applicant: Maxwell Rennie, Irvine, CA (US)

(72) Inventor: Maxwell Rennie, Irvine, CA (US)

(*) Notice: Subject to any disclaimer, the term of this patent is extended or adjusted under 35 U.S.C. 154(b) by 252 days.

(21) Appl. No.: 15/976,873

(22) Filed: May 11, 2018

(65) Prior Publication Data

US 2019/0345077 A1 Nov. 14, 2019

(51) Int. Cl.
*C06F 1/06* (2006.01)
*C06F 3/02* (2006.01)
*A61K 36/18* (2006.01)
*A61M 21/00* (2006.01)

(52) U.S. Cl.
CPC .............. *C06F 1/06* (2013.01); *A61K 36/18* (2013.01); *C06F 3/02* (2013.01); *A61M 2021/0016* (2013.01)

(58) Field of Classification Search
CPC ...... C06F 1/00; C06F 1/02; C06F 1/06; C06F 1/26
USPC .......................................... 144/50, 52, 54, 58
See application file for complete search history.

(56) References Cited

U.S. PATENT DOCUMENTS

| 992,586 | A | * | 5/1911 | Paulson | C06F 1/08 144/58 |
| 4,072,473 | A | * | 2/1978 | Radkowski | B05C 9/06 144/51 |
| 9,301,910 | B2 | | 4/2016 | Yontz | |
| 9,408,935 | B2 | | 8/2016 | Levine | |
| 2011/0274643 | A1 | | 11/2011 | Yontz | |
| 2011/0300198 | A1 | | 12/2011 | Nussinovitch et al. | |
| 2015/0133565 | A1 | | 5/2015 | Yao et al. | |
| 2015/0346193 | A1 | | 12/2015 | Plant | |
| 2016/0346339 | A1 | | 12/2016 | Finley et al. | |
| 2019/0282642 | A1 | * | 9/2019 | Meeusen | A61K 36/185 |

* cited by examiner

*Primary Examiner* — Matthew Katcoff
(74) *Attorney, Agent, or Firm* — Select Patents; Ashkon Cyrus

(57) ABSTRACT

The present invention pertains generally toward an easier and more efficient way to burn Palo Santo wood for aromatherapy, and more particularly toward a self-lighting match stick made of Palo Santo wood. In the present invention, the wood of Palo Santo is turned into match stick by covering the small sticks of Palo Santo with paraffin wax and match head solution. The present invention enables easy ignition of the Palo Santo wood by the user for aromatherapy and makes the process hassle free.

1 Claim, 2 Drawing Sheets

SELF-LIGHTING PALO SANTO COMBUSTIBLE ARTICLE AND METHOD OF MANUFACTURE THEREOF

FIELD OF THE INVENTION

The present invention pertains generally toward an easier and more efficient way to burn Palo Santo wood for aromatherapy, and more particularly toward a self-lighting match stick made of Palo Santo wood.

BACKGROUND OF THE INVENTION

Typical Palo Santo commercial products are formed of a large stick which is intended to be burned with a flame. These available commercial products may be used in aromatherapy and naturopathic medicine and require a long time for the wood to burn effectively. After the burning has reached full flame, the flame is typically blown out by the user. The amount of smoke released may be more than desired. There may also be unpleasant odor from the lighter, as well as heavy smoke produced when a substantial amount of the wood has been burned, which is environmentally unsound.

There is, accordingly, a need for an improved approach to burning Palo Santo wood that does not require the use of a lighter or take as much time. The improved match stick should be primarily configured for use in specific aromatherapy applications. The present invention fulfills this need, and further provides related advantages.

SUMMARY OF THE INVENTION

In order to overcome the drawbacks of the prior art, the present invention provides a combustible article comprising Palo Santo that is readily and quickly ignited, and then smolders and releases smoke from the area that is aflame.

The present invention further provides a method of making an improved combustible article, wherein the method comprises cutting a large stick of Palo Santo wood into a plurality small sticks of about 2×0.25×0.25 inches; dipping the plurality of small sticks into a wax such as a paraffin wax, heating in an oven the plurality of small sticks in an oven configured to melt the wax, such that the sticks are dipped half an inch with the wax; and dipping a tip of paraffin wax covered sticks into a match head solution.

Other features and advantages of the present invention will be apparent from the following more detailed description of the preferred embodiment, taken in conjunction with the accompanying drawings, which illustrate, by way of example, the principles of the invention. The scope of the invention is not, however, limited to this preferred embodiment.

BRIEF DESCRIPTION OF THE DRAWINGS

The following drawings illustrate exemplary embodiments. They are helpful in illustrating objects, features and advantages of the present invention. That is, the present invention will be more apparent from the following detailed description taken in conjunction with accompanying drawings.

DETAILED DESCRIPTION OF THE INVENTION

Figure 1:
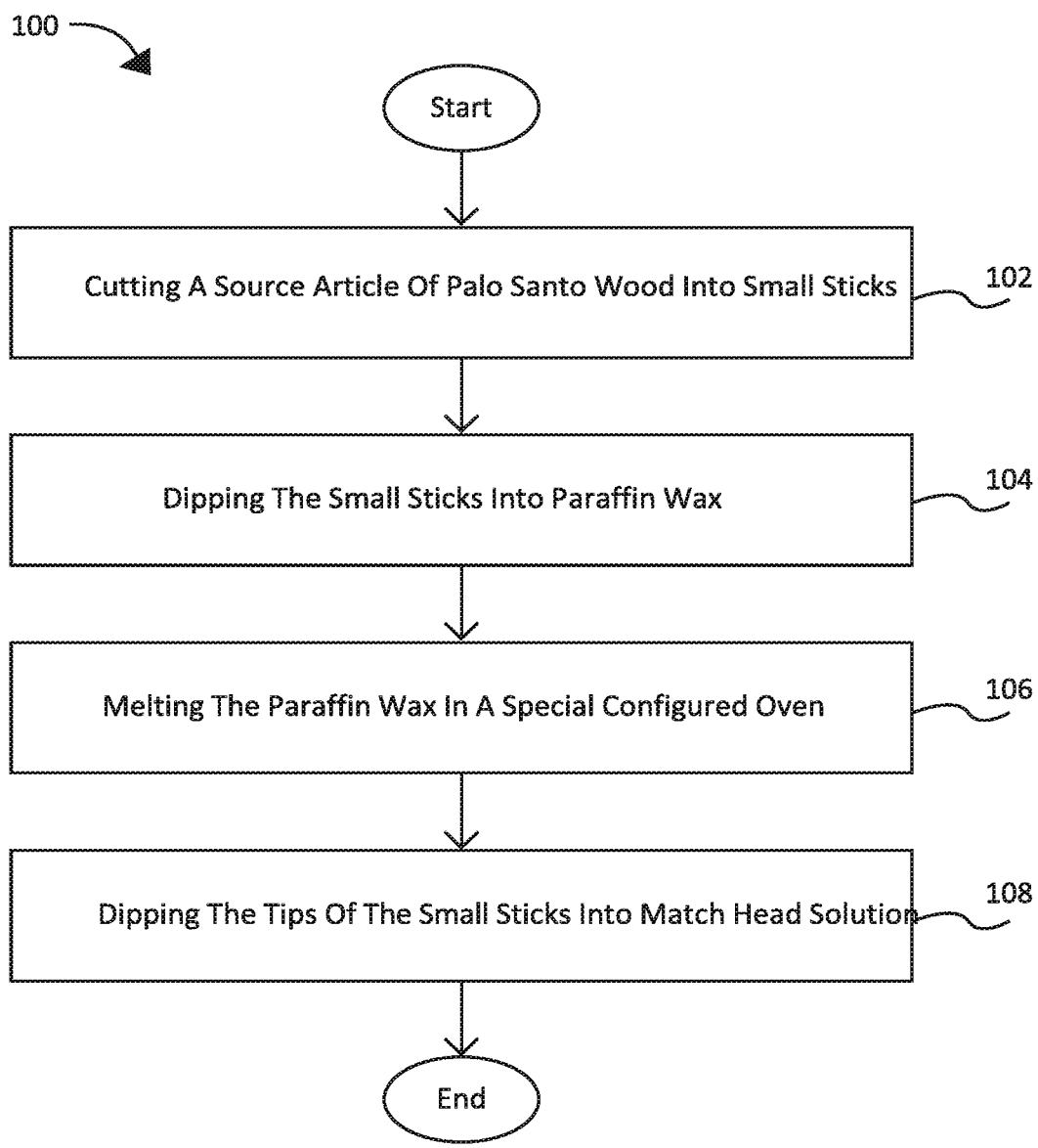
FIG. 1 illustrates a method of making an improved combustible article.

Reference will now be made in detail to exemplary embodiments of the present invention, examples of which are illustrated in the accompanying drawings. Whenever possible, the same reference numerals will be used throughout the drawings to refer to the same or like parts.

References to "one embodiment," "at least one embodiment," "an embodiment," "one example," "an example," "for example," indicate that the embodiment(s) or example(s) may include a particular feature, structure, characteristic, property, element, or limitation but that not every embodiment or example necessarily includes that particular feature, structure, characteristic, property, element, or limitation. Further, repeated use of the phrase "in an embodiment" does not necessarily refer to the same embodiment.

FIG. 1 illustrates a process 100 of the given invention which is also a preferred embodiment of the invention.

In Step 102, a large stick of Palo Santo wood is cut into small sticks of a predetermined length configured to provide an optimal burning experience. In one embodiment, a large stick of Palo Santo wood is cut into small sticks so that it is generally the length of a match stick. The length of the stick depends on the user, a minimum length is about 2×0.25×0.25 inches. It can be appreciated that this length ensures that sticks burns properly, without causing any harm to the user at the time of ignition.

In step 104, the small sticks are dipped into a wax. In one embodiment, the wax used for properly coating the sticks with paraffin wax. In one embodiment, the small sticks are dipped approximately 0.5 inches into the paraffin wax. The paraffin wax ensures that the flame burns down past the head to the stick.

Step 106 comprises melting the paraffin wax by putting the small sticks into oven. The paraffin wax coated small sticks are then heated in an oven configured to melt the paraffin wax. It provides a small amount of fuel to transfer the flame from the tip to the matchstick.

Step 108 comprises dipping the tip of small sticks into a match head solution. In one embodiment, the match head solution comprises sulfur and potassium chlorate. The potassium chlorate acts as an oxidizing agent (bringing in an effective amount of oxygen for the fuel) and the sulfur acts as the fuel that burns. This creates the final match stick product In one embodiment, the final match stick product can be used in aromatherapy settings. The Palo Santo match sticks are either ignited by frictional heat generated by striking the match against a suitable surface, or can be ignited by a lighter.

It can be appreciated that due to the configured size, the final Palo Santo match sticks product may readily and quickly ignited, and then smolders and releases smoke from the area that is aflame.

The smoke released from the Palo Santo wood includes phytochemicals called terpenes, including limonene and α-terpineol, which may be effective for fighting free radical damage (also called oxidative stress), relieving stomach aches, fighting stress, reducing pains due to arthritis and healing many other conditions. Other benefits include odor elimination and relaxation.

In one embodiment, the major constituents of the Palo santo are Limonene, α-Terpineol, Menthofuran, Carvone. Germacrene D, γ-Muurolene, trans-Carveol, and Pulegone.

Figure 2:
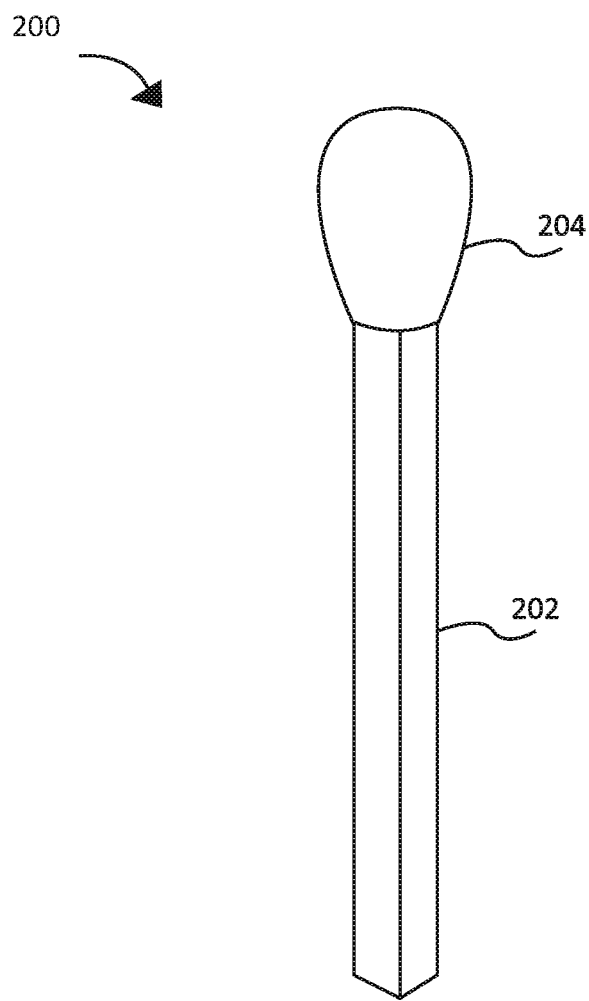
FIG. 2 illustrates a perspective view of a combustible article prepared according to the invention.

FIG. 2 illustrates the schematic view of the given invention (200). Herein, the small sticks of Palo Santo (202), wherein the size of the stick is about 2/0.25/0.25 inches, is covered with paraffin wax (not shown) and a match head solution (204).

Although the invention has been explained in relation to a preferred embodiment, it is to be understood that many other possible modifications and variation scan be made without departing from the spirit and scope of the invention. The invention should not be limited as such, except as described in the following claims.

In addition, the foregoing description sets forth structure for a Palo Santo match stick in accordance with various aspects of the invention. The invention also pertains to the manufacture of such embodiments. While the invention has been described in detail above with reference to numerous embodiments, variations within the scope and spirit of the invention will be apparent to those of ordinary skill in the art. Thus, the invention should be considered as limited only by the scope of the appended claims.

The invention claimed is:

1. A method of making an improved combustible article, wherein the method comprises:
   cutting a large stick of Palo Santo wood into a plurality small sticks, wherein each of the plurality of small sticks is a dimension of about 2×0.25×0.25 inches;
   dipping the plurality of small sticks into paraffin wax;
   heating in the plurality of small sticks in an oven configured to melt the paraffin wax, such that the sticks are covered approximately half an inch with the paraffin wax; and
   dipping a tip of paraffin wax covered sticks into a match head solution to create a plurality of Palo Santo match sticks configured for use in aromatherapy, wherein the Palo Santo match sticks are configured to release terpenes from the Palo Santo wood.

* * * * *